United States Patent
Kozai

(10) Patent No.: US 12,002,201 B2
(45) Date of Patent: Jun. 4, 2024

(54) ULTRASONIC DIAGNOSTIC DEVICE, OPERATION METHOD OF ULTRASONIC DIAGNOSTIC DEVICE, AND COMPUTER READABLE RECORDING MEDIUM

(71) Applicant: OLYMPUS CORPORATION, Tokyo (JP)

(72) Inventor: Shigenori Kozai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 407 days.

(21) Appl. No.: 17/382,604

(22) Filed: Jul. 22, 2021

(65) Prior Publication Data
US 2021/0350536 A1   Nov. 11, 2021

Related U.S. Application Data

(63) Continuation of application No. PCT/JP2019/005244, filed on Feb. 14, 2019.

(51) Int. Cl.
*G06T 7/00* (2017.01)
*A61B 8/00* (2006.01)

(52) U.S. Cl.
CPC ........... *G06T 7/0012* (2013.01); *A61B 8/463* (2013.01); *G06T 2207/10132* (2013.01); *G06T 2207/20076* (2013.01); *G06T 2207/20081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2005/0020903 A1 | 1/2005 | Krishnan et al. | |
| 2014/0309530 A1 | 10/2014 | Chono | |
| 2018/0011980 A1 | 1/2018 | Contu et al. | |
| 2019/0025280 A1* | 1/2019 | Kaditz | .................. G16H 50/50 |

FOREIGN PATENT DOCUMENTS

| | | |
|---|---|---|
| JP | 2007-527743 A | 10/2007 |
| JP | 2013-162810 A | 8/2013 |
| JP | 6181542 B2 | 8/2017 |
| JP | 2018-503902 A | 2/2018 |
| WO | 2012/161040 A1 | 11/2012 |

OTHER PUBLICATIONS

International Search Report dated May 7, 2019 received in PCT/JP2019/005244.

* cited by examiner

*Primary Examiner* — Leon Flores
(74) *Attorney, Agent, or Firm* — Scully, Scott, Murphy & Presser, P.C.

(57) ABSTRACT

An ultrasonic diagnostic device includes a processor including hardware, the processor being configured to: analyze a first examination performed on a subject using first ultrasound image data of an ultrasound image of the subject to be diagnosed; calculate a rate of accuracy of diagnosis in a case where a second examination is performed on the subject based on an analysis result of the first examination performed on the subject, analysis results of the first examination performed on a plurality of sample subjects, and analysis results of the second examination performed on the plurality of sample subjects; and control a display device to display the rate of accuracy of diagnosis.

7 Claims, 4 Drawing Sheets

FIG.2A

| SUBJECT No. | FIRST EXAMINATION (MODE B IMAGE) | SECOND EXAMINATION (CONTRAST ENHANCED EUS IMAGE) | THRESHOLD (80%) |
|---|---|---|---|
| 1 | 60% | 95% | ○ |
| 2 | 30% | 40% | × |
| 3 | 55% | 80% | ○ |
| 4 | 60% | 85% | ○ |
| 5 | 40% | 30% | × |
| 6 | 60% | 70% | × |
| 7 | 20% | 40% | × |
| 8 | 90% | 85% | ○ |
| 9 | 75% | 65% | × |
| 10 | 60% | 65% | × |

FIG.2B

| SUBJECT No. | FIRST EXAMINATION (MODE B IMAGE) | SECOND EXAMINATION (BIOPSY IMAGE) | THRESHOLD (80%) |
|---|---|---|---|
| 1 | 50% | 45% | × |
| 2 | 45% | 30% | × |
| 3 | 80% | 85% | ○ |
| 4 | 60% | 80% | ○ |
| 5 | 60% | 90% | ○ |
| 6 | 75% | 60% | × |
| 7 | 10% | 25% | × |
| 8 | 20% | 10% | × |
| 9 | 50% | 60% | × |
| 10 | 45% | 50% | × |

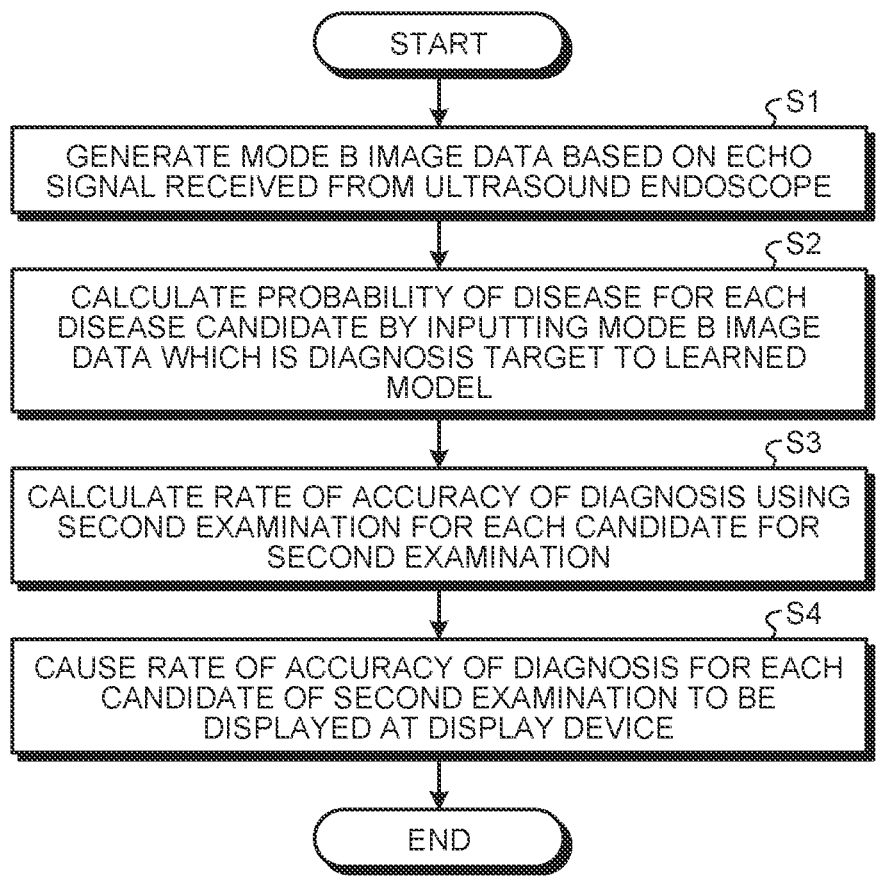

FIG.5

| DISEASE CANDIDATE | PROBABILITY |
|---|---|
| PANCREATIC CANCER | 30% |
| pNET | 45% |
| CHRONIC PANCREATITIS | 20% |
| SOUNDNESS | 5% |

ULTRASONIC DIAGNOSTIC DEVICE, OPERATION METHOD OF ULTRASONIC DIAGNOSTIC DEVICE, AND COMPUTER READABLE RECORDING MEDIUM

This application is a continuation of International Application No. PCT/JP2019/005244, filed on Feb. 14, 2019, the entire contents of which are incorporated herein by reference.

BACKGROUND

The present disclosure relates to an ultrasonic diagnostic device, an operation method of the ultrasonic diagnostic device, and a computer readable recording medium.

In the related art, it has been known a technique of establishing a series of subsequent examination procedure through predetermined statistical analysis based on comparison between stored operation history and operation content, and the latest operation or recently performed examination content input by an operator.

SUMMARY

According to one aspect of the present disclosure, there is provided an ultrasonic diagnostic device including a processor including hardware, the processor being configured to: analyze a first examination performed on a subject using first ultrasound image data of an ultrasound image of the subject to be diagnosed; calculate a rate of accuracy of diagnosis in a case where a second examination is performed on the subject based on an analysis result of the first examination performed on the subject, analysis results of the first examination performed on a plurality of sample subjects, and analysis results of the second examination performed on the plurality of sample subjects; and control a display device to display the rate of accuracy of diagnosis.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 2A is a view illustrating a first example of a table stored in a table storage unit;

FIG. 2E is a view illustrating a second example of a table stored in a table storage unit;

FIG. 3 is a flowchart illustrating outline of processing performed by the ultrasonic diagnostic device according to the embodiment;

FIG. 4 is a view illustrating a display example of rates of accuracy of diagnosis for candidates for a second examination displayed at a display device; and FIG. 5 is a view illustrating a display example of probabilities for each disease candidate in a first examination displayed at the display device.

DETAILED DESCRIPTION

Figure 1:
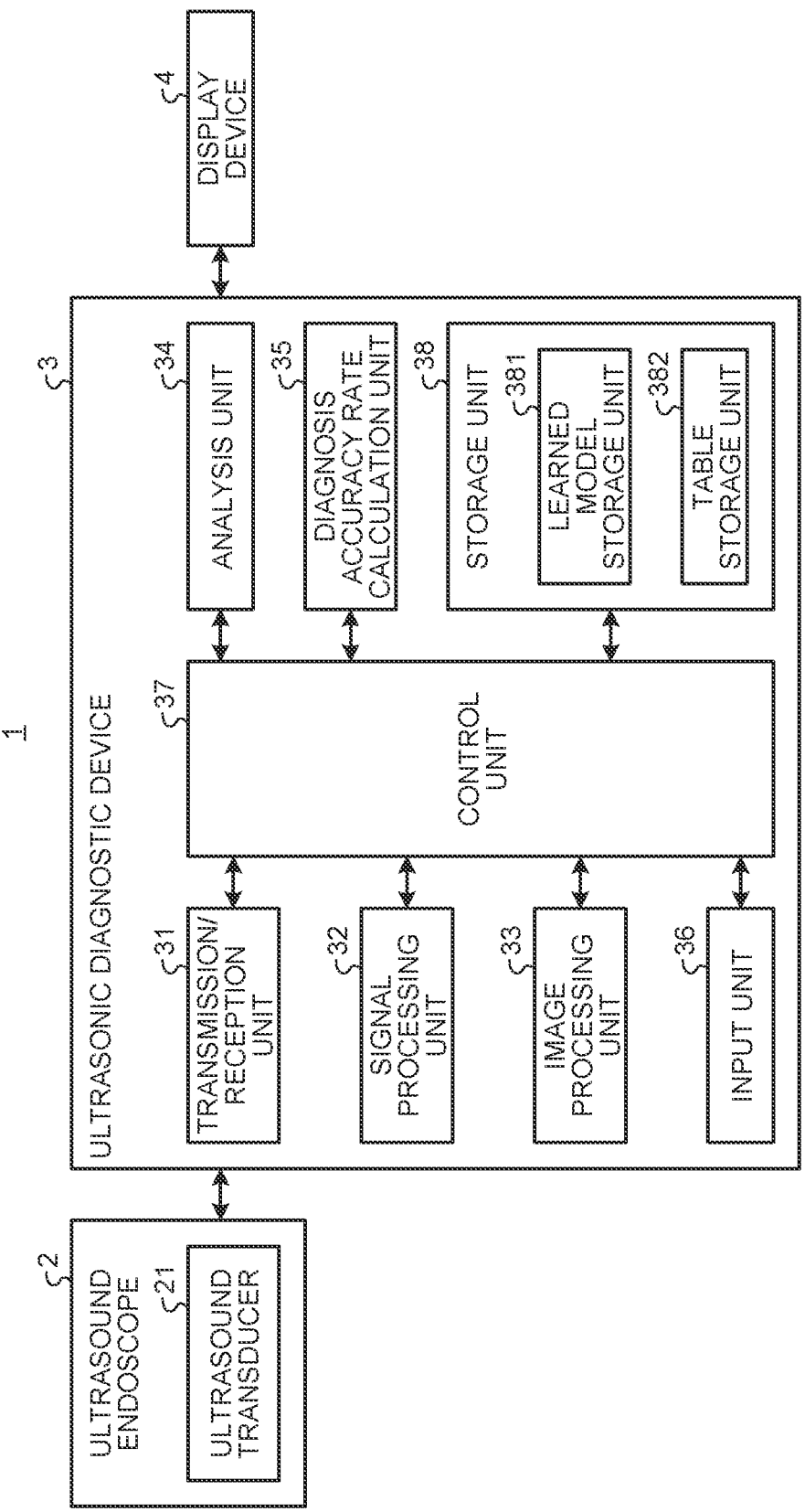
FIG. 1 is a block diagram illustrating a configuration of an ultrasonic diagnostic system including an ultrasonic diagnostic device according to an embodiment.

An embodiment for implementing the present disclosure (hereinafter, referred to as an "embodiment") will be described below with reference to the accompanying drawings.

FIG. 1 is a block diagram illustrating a configuration of an ultrasonic diagnostic system including an ultrasonic diagnostic device according to an embodiment. An ultrasonic diagnostic system 1 illustrated in FIG. 1 includes an ultrasound endoscope 2, an ultrasonic diagnostic device 3, and a display device 4.

The ultrasound endoscope 2 is inserted into the body of a subject, transmits an ultrasonic wave to the subject, and receives the ultrasonic wave reflected at the subject. An ultrasound transducer 21 is provided at a distal end portion of the ultrasound endoscope 2. The ultrasound transducer 21 converts an electrical pulse signal received from the ultrasonic diagnostic device 3 into an ultrasonic pulse (acoustic pulse), irradiates the subject with the ultrasonic pulse, converts an ultrasonic echo reflected at the subject into an electrical echo signal (ultrasonic signal) which expresses the ultrasonic echo with voltage change, and outputs the electrical echo signal. The ultrasound transducer 21 may be any type among a convex ultrasound transducer, a linear ultrasound transducer, a radial ultrasound transducer, or the like. Further, the ultrasound transducer 21 may be a transducer which mechanically scans the subject or may be a transducer which electronically scans the subject. The ultrasound endoscope 2 is to observe subjects such as, for example, a digestive tract (esophagus, stomach, duodenum, large intestine) and respiratory organs (trachea, bronchi) of the subject, and has different radiuses of an insertion portion and sizes and types of the ultrasound transducer 21 in accordance with the subject to be observed.

A treatment tool channel which is a conduit for allowing insertion of a treatment tool such as a puncture needle is formed inside the insertion portion of the ultrasound endoscope 2. An opening portion on a proximal end side of the treatment tool channel is positioned at an intermediate part of the insertion portion, while an opening portion on a distal end side of the treatment tool channel is positioned near the ultrasound transducer 21.

The ultrasound endoscope 2 may include an imaging unit configured to capture an image of the subject to generate image data, and a light guide configured to guide illumination light radiated to the subject to a distal end of the insertion portion. In this case, a proximal end portion of the light guide is connected to a light source device including a light source which generates illumination light. Note that the ultrasonic diagnostic device 3 and the light source device may be integrally constituted.

The ultrasonic diagnostic device 3 includes a transmission/reception unit 31, a signal processing unit 32, an image processing unit 33, an analysis unit 34, a diagnosis accuracy rate calculation unit 35, an input unit 36, a control unit 37 and a storage unit 38.

The transmission/reception unit 31, which is electrically connected to the ultrasound endoscope 2, transmits a transmission signal (pulse signal) including a high voltage pulse to the ultrasound transducer 21 based on a predetermined waveform and a predetermined transmission timing. Further, the transmission/reception unit 31 receives an echo signal which is an electrical reception signal from the ultrasound transducer 21, generates data of a high frequency (RF: radio frequency) digital signal (hereinafter, referred to as RF data) and outputs the RF data.

The transmission/reception unit 31 transmits various kinds of control signals output from the control unit 37 to the ultrasound endoscope 2, receives information including an ID for identification from the ultrasound endoscope 2 and outputs the information to the control unit 37.

The signal processing unit 32 generates digital received data for mode B based on the RF data received from the transmission/reception unit 31. Specifically, the signal processing unit 32 performs publicly known processing such as a bandpass filter, envelope detection, logarithmic transformation and attenuation correction on the RF data to generate digital received data for mode B and outputs the generated received data for mode B corresponding to one frame to the image processing unit 33.

The image processing unit 33 generates mode B image data based on the received data for mode B received from the signal processing unit 32. The image processing unit 33 generates mode B image data by performing signal processing such as scan converter processing, gain processing and contrast processing on the received data for mode B output from the signal processing unit 32 and decimating the data in accordance with a data step width determined in accordance with a display range of the image at the display device 4. The mode B image is a grayscale image in which values of R (red), G (green) and B (blue) which are variables are made the same in a case where an RGB color system is employed as color space.

The image processing unit 33 also generates various kinds of image data in accordance with examination items, such as a contrast enhanced EUS image, a tissue characterization image and elastography as well as the mode B image data.

The analysis unit 34 analyzes a predetermined first examination performed on the subject based on an ultrasound image of the subject to be diagnosed. For example, in a case where the first examination is an examination using the mode B image, the analysis unit 34 calculates a probability of a disease of the subject for each disease candidate based on the mode B image of the subject to be diagnosed. In this event, the analysis unit 34 calculates the probability of a disease of the subject by inputting the mode B image data of the subject to be diagnosed to a learned model as an input parameter. The learned model is a model generated through machine learning using the mode B image data of a plurality of subjects and diagnosis results obtained using respective pieces of the mode B image data as supervised data and is stored in a learned model storage unit 381 of the storage unit 38.

The diagnosis accuracy rate calculation unit 35 calculates a rate of accuracy of diagnosis using a second examination performed on the subject to be diagnosed based on the analysis result of the analysis unit 34, analysis results of the first examination performed on other subjects and analysis results of the second examination performed on other subjects. The second examination is different from the first examination. The diagnosis accuracy rate calculation unit 35 calculates a rate of accuracy of diagnosis in accordance with candidates for the second examination with reference to a table stored in a table storage unit 382 of the storage unit 38.

The input unit 36, which is implemented using a user interface such as a keyboard, a mouse, a trackball, a touch panel and a microphone, accepts input of various kinds of information. The input unit 36 outputs the accepted information to the control unit 37.

The control unit 37 collectively controls the ultrasonic diagnostic system 1 including the ultrasonic diagnostic device 3 by reading out information stored in the storage unit 38 from the storage unit 38 and executing various kinds of computation processing relating to an operation method of the ultrasonic diagnostic device 3.

The storage unit 38 includes the learned model storage unit 381 which stores a learned model to be used by the analysis unit 34 to perform computation, and the table storage unit 382 which stores a table to be used by the diagnosis accuracy rate calculation unit 35 to calculate a rate of accuracy of diagnosis. Further, the storage unit 38 stores various kinds of programs for operating the ultrasonic diagnostic device 3, and data including various kinds of parameters, or the like, required for operation of the ultrasonic diagnostic device 3.

The learned model stored in the learned model storage unit 381 is a model generated through, for example, deep learning using a neural network including a plurality of intermediate layers. This learned model uses a set of mode B image data of a subject for learning and a result of diagnosis (whether or not the subject has a disease) using the mode B image data, as supervised data. More specifically, the learned model is generated by determining network parameters such as weight, bias, or the like, of nodes of a neural network using a plurality of pieces of supervised data. For example, a convolutional neural network further including a convolutional layer and a pooling layer may be used as the neural network.

FIGS. 2A and 2B are views illustrating examples of a table stored in a table storage unit 382. In FIG. 2A and FIG. 2B, the first examination is an examination using the mode B image, and probabilities of a predetermined disease candidate (for example, cancer) are indicated. Note that the table storage unit 382 stores similar tables for each disease candidate.

A table 101 indicated in FIG. 2A is a table in a case where the second examination is an examination using a contrast enhanced EUS image. The table 101 includes probabilities of a disease based on the mode B image data, probabilities of a disease based on the contrast enhanced EUS image and information as to whether or not the probabilities of a disease based on the contrast enhanced EUS image are equal to or higher than a threshold, for each sample subject.

A table 102 indicated in FIG. 2B is a table in a case where the second examination is an examination using a biopsy image. The biopsy image is an image obtained by capturing an image of a body tissue taken by inserting a puncture needle into the treatment tool channel of the ultrasound endoscope 2 and puncturing an organ of the sample subject. The table 102 includes probabilities of a disease based on the mode B image, probabilities of a disease based on the biopsy image, and information as to whether or not the probabilities of a disease based on the biopsy image exceed a threshold, for each sample subject.

The probabilities in the tables 101 and 102 are obtained in advance through machine learning. For example, the probabilities of a disease calculated in the examination using the mode B image are calculated using the learned model generated by performing deep learning using supervised data including a set of the mode B image data and the diagnosis result in accordance with the mode B image data in a similar manner to the learned model described above. Further, the probabilities of a disease calculated in the examination using the contrast enhanced EUS image are calculated using the learned model generated by performing deep learning using supervised data including a set of the contrast enhanced EUS image data and the diagnosis result in accordance with the contrast enhanced EUS image data. Further, the probabilities of a disease calculated in the examination using the biopsy image are calculated using the learned model generated by performing deep learning using supervised data including a set of the biopsy image data and the diagnosis result in accordance with the biopsy image data. Note that the learned models are different for each input image. The probabilities of a disease in the tables 101 and 102 are probabilities of a disease obtained as output parameters in a case where the mode B image data, the contrast enhanced EUS image data and the biopsy image data are respectively input to the learned models for each subject. Note that the learned model which outputs a range of the probability (for example, 70% to 80%) instead of outputting the probability of a disease with a specific value may be used.

The threshold of the probability of disease in the tables 101 and 102 is set at 80% as an example, and "∘" is indicated in a case where the probability is equal to or higher than 80%, and "x" is indicated in a case where the probability is lower than 80%. This threshold may be able to be changed by a user through input from the input unit 36. Note that the threshold may be changed for each second disease candidate or the images may be differently weighted for each second disease candidate. For example, the biopsy image is obtained by capturing an image of a tissue acquired using the puncture needle, and thus, the biopsy image may be less weighted than the contrast enhanced EUS image in view of load of the biopsy image on the subject being higher than load of the contrast enhanced EUS image. Further, the number of subjects described in the tables may be larger than the number (10) indicated in FIG. 2A and FIG. 2B as an example.

Note that while the supervised data in a case where the learned model is generated is different from various kinds of image data input in a case where the tables 101 and 102 are generated, the same image data may be partly used. Further, while a case is described here as an example where a candidate for the second examination is an examination using the contrast enhanced EUS image and an examination using the biopsy image, examples of the candidate for the second examination may include color flow, tissue characterization, elastography, or the like.

The storage unit 38 includes a read only memory (ROM) in which various kinds of programs, or the like, including an operation program for executing the operation method of the ultrasonic diagnostic device 3 are installed in advance, and a random access memory (RAM) in which operation parameters, data, or the like, of respective kinds of processing, or the like, are stored. The operation program may be widely distributed by being recorded in a computer readable recording medium such as a hard disk, a flash memory, a CD-ROM, a DVD-ROM and a flexible disk. Note that the ultrasonic diagnostic device 3 may acquire various kinds of programs by downloading the programs via a communication network. The communication network described here is implemented by, for example, an existing public switched telephone network, a local area network (LAN) or a wide area network (WAN) and may be either a wired network or a wireless network.

The ultrasonic diagnostic device 3 having the above-described configuration includes one or more pieces of hardware such as a central processing unit (CPU), a graphics processing unit (GPU), an application specific integrated circuit (ASIC) and a field programmable gate array (FPGA).

The display device 4, which is constituted with a liquid crystal, an organic electro luminescence (EL), or the like, receives data such as an ultrasound image generated by the ultrasonic diagnostic device 3 and displays the image or displays a calculation result of the diagnosis accuracy rate calculation unit 35.

FIG. 3 is a flowchart illustrating outline of processing performed by the ultrasonic diagnostic device 3. First, the ultrasonic diagnostic device 3 generates mode B image data based on the echo signal received from the ultrasound endoscope 2 inserted into the subject to be diagnosed (Step S1). Specifically, the transmission/reception unit 31 receives the echo signal from the ultrasound endoscope 2 and outputs RF data, the signal processing unit 32 generates received data for mode B based on the RF data, and the image processing unit 33 generates mode B image data based on the received data for mode B.

Subsequently, the analysis unit 34 calculates a probability of a disease for each disease candidate by inputting the mode B image data which is a diagnosis target to the learned model (Step S2). The mode B image data which is a diagnosis target input here may be the mode B image data selected by the user through the input unit 36 or may be the mode B image data selected at a predetermined timing or at a predetermined time interval. Note that in a case where a specific disease is selected in advance, the analysis unit 34 may calculate a probability of only the disease.

Then, the diagnosis accuracy rate calculation unit 35 calculates the rate of accuracy of diagnosis using the second examination for each candidate for the second examination based on the analysis result of the analysis unit 34 (Step S3). For example, in a case where the candidate for the second examination is an examination using the contrast enhanced EUS image, in a case where the probability of the disease calculated by the analysis unit 34 is 60%, the diagnosis accuracy rate calculation unit 35 calculates a rate of the subjects for which probabilities that the subjects are diagnosed as having a disease using the contrast enhanced EUS image being equal to or higher than a threshold (80%) among the data described in the table 101 indicated in FIG. 2A as the rate of accuracy of diagnosis with reference to subjects No. 1, 4, 6 and 10. Specifically, the subjects No. 1 and 4 among the four subjects satisfy conditions, and thus, the diagnosis accuracy rate calculation unit 35 calculates the rate of accuracy of diagnosis as 2/4=50(%). In a similar manner, in a case where the candidate for the second examination is an examination using the biopsy image, in a case where the probability of the disease calculated by the analysis unit 34 is 60%, the diagnosis accuracy rate calculation unit 35 calculates the rate of accuracy of diagnosis in a case where the candidate for the second examination is an examination using the biopsy image as 2/2=100(%) with reference to the table 102 indicated in FIG. 2B.

After Step S3, the control unit 37 causes the rate of accuracy of diagnosis for each candidate of the second examination calculated by the diagnosis accuracy rate calculation unit 35 to be displayed at the display device 4 (Step S4). FIG. 4 is a view illustrating a display example of the rates of accuracy of diagnosis displayed at the display device 4. The display device 4 displays the rates of accuracy of diagnosis for each candidate for the second examination as illustrated in a table 103 in FIG. 4.

According to the embodiment described above, the rate of accuracy of diagnosis in a case where the second examination is performed on the subject to be diagnosed is calculated based on the analysis result of the first examination performed on the subject using the ultrasound image of the subject to be diagnosed, the analysis results of the first examination performed on a plurality of sample subjects, and the analysis results of the second examination performed on the plurality of sample subjects, and the calculation result is displayed at the display device, so that a user such as a surgeon may grasp the rate of accuracy of diagnosis of the second examination, which may support selection of examination content to be performed next in accordance with the disease candidate found in the examination. As a result, next examination means which is more effective may be presented to the user. In other words, suspected diseases may be narrowed down with as few examinations as possible, so that it is possible to reduce physical, temporal and cost load on a patient.

FIG. 5 is a view illustrating a display example of the display device 4 in a modified example of the embodiment. In the present modified example, after the analysis unit 34 calculates probabilities of diseases for each disease candidate, the control unit 37 causes the probabilities of the diseases to be displayed at the display device 4. A table 104 indicated in FIG. 5 indicates a display example of a table displayed at the display device 4. The table 104 indicates a case where probabilities of pancreatic cancer, pNET and chronic pancreatitis which are three disease candidates are respectively 30%, 45% and 20%, and a probability of soundness is 5%. In this case, in a case where the user selects and inputs one of the three disease candidates from the input unit 36, the control unit 37 causes rates of accuracy of diagnosis of candidates for the second examination calculated for the selected disease candidate to be displayed at the display device 4. In this event, display content of the display device 4 is similar to the table 103 indicated in FIG. 4. Note that the control unit 37 may cause name of candidates for the second examination for which the rates of accuracy of diagnosis are equal to or higher than a predetermined rate of accuracy to be displayed at the display device 4 in place of the table 104.

According to the modified example of the embodiment described above, it is possible to allow the user to grasp the rate of accuracy of diagnosis in the second examination for each disease candidate.

While the embodiment for implementing the present disclosure has been described above, the present disclosure is not limited only to the above-described embodiment.

For example, the analysis unit 34 may analyze parameters such as feature data in an image in place of the probability of the disease. In this case, the diagnosis accuracy rate calculation unit 35 only requires to calculate the rate of accuracy of diagnosis in the second examination based on relationship between values of the parameters and diseases.

Further, the ultrasonic diagnostic device 3 may include a learning unit configured to automatically update network parameters of a learned model stored in the learned model storage unit 381 using the image data acquired from the ultrasonic diagnostic device 3 and a diagnosis result based on the image data.

Further, the ultrasonic diagnostic device 3 may receive an upgraded learned model from other equipment communicatively connected via a communication network and update the learned model stored in the learned model storage unit 381.

Further, a learned model generated through machine learning other than deep learning may be used. Examples of machine learning other than deep learning may include support vector machine, a decision tree, or the like.

In this manner, the present disclosure may include various embodiments, or the like, within a scope not deviating from technical idea recited in the claims.

According to the present disclosure, it is possible to support selection of an examination which should be performed next in accordance with disease candidates found in an examination.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic device comprising
a processor comprising hardware, the processor being configured to:
analyze a first examination performed on a subject using first ultrasound image data of an ultrasound image of the subject to be diagnosed;
calculate a rate of accuracy of diagnosis in a case where a second examination is performed on the subject based on an analysis result of the first examination performed on the subject, analysis results of the first examination performed on a plurality of sample subjects, and analysis results of the second examination performed on the plurality of sample subjects; and
control a display device to display the rate of accuracy of diagnosis;
wherein the processor is configured to calculate the rate of accuracy by:
calculating a probability of a disease of the subject based on the first examination; and
calculating the rate of accuracy of diagnosis using the probability of the disease of the subject and probabilities of diseases of the sample subjects based on the first examination and the second examination.

2. The ultrasonic diagnostic device according to claim 1, wherein the processor is configured to calculate a rate of sample subjects for which probabilities of diseases based on the second examination are equal to or higher than a threshold among the sample subjects for which probabilities of diseases based on the first examination are a same as the probability of disease of the subject to be diagnosed and calculates the rate of accuracy of diagnosis using the calculated rate.

3. The ultrasonic diagnostic device according to claim 1, further comprising an input unit configured to accept input of information, wherein
the processor is configured to:
analyze the first examination for each disease candidate,
calculate the rate of accuracy of diagnosis for each disease candidate;
control the display device to display an analysis result for each disease candidate; and
control, in a case where the input unit accepts input of selection of one disease candidate, the display device to display the rate of accuracy of diagnosis for the selected disease candidate.

4. The ultrasonic diagnostic device according to claim 1, wherein the processor is configured to analyze the first examination by inputting the first ultrasound image data to a learned model generated through machine learning.

5. The ultrasonic diagnostic device according to claim 4, wherein the learned model is a model learned by using second ultrasound image data and a diagnosis based on the second ultrasound image data.

6. An operation method of an ultrasonic diagnostic device, comprising:
analyzing a first examination performed on a subject using first ultrasound image data of an ultrasound image of the subject to be diagnosed;
calculating a rate of accuracy of diagnosis in a case where a second examination is performed on the subject based on an analysis result of the first examination performed on the subject, analysis results of the first examination performed on a plurality of sample subjects, and analysis results of the second examination performed on the plurality of sample subjects; and controlling a display device to display the rate of accuracy of diagnosis;

wherein the calculating of the rate of accuracy comprises:
    calculating a probability of a disease of the subject based on the first examination; and
    calculating the rate of accuracy of diagnosis using the probability of the disease of the subject and probabilities of diseases of the sample subjects based on the first examination and the second examination.

7. A non-transitory computer-readable recording medium on which an executable program is recorded, the program causing a processor of a computer to execute:

analyzing a first examination performed on a subject using first ultrasound image data of an ultrasound image of the subject to be diagnosed;

calculating a rate of accuracy of diagnosis in a case where a second examination is performed on the subject based on an analysis result of the first examination performed on the subject, analysis results of the first examination performed on a plurality of sample subjects, and analysis results of the second examination performed on the plurality of sample subjects; and controlling a display device to display the rate of accuracy of diagnosis;

wherein the calculating of the rate of accuracy comprises:
    calculating a probability of a disease of the subject based on the first examination; and
    calculating the rate of accuracy of diagnosis using the probability of the disease of the subject and probabilities of diseases of the sample subjects based on the first examination and the second examination.

* * * * *